United States Patent [19]

Peugh

[11] Patent Number: 5,416,923
[45] Date of Patent: May 23, 1995

[54] REMOVABLE NOSE SUN SHIELD FOR EYEGLASSES

[76] Inventor: John L. Peugh, 230 La Veta Ave., Encinitas, Calif. 92024

[21] Appl. No.: 155,525

[22] Filed: Nov. 22, 1993

[51] Int. Cl.⁶ ............................................. A41D 13/00
[52] U.S. Cl. ....................................................... 2/9; 2/206
[58] Field of Search ................. 2/13, 9, 206, 909, 918, 2/12, 2, 424, 446; 351/41, 131–132, 138

[56] References Cited

U.S. PATENT DOCUMENTS

| | | | |
|---|---|---|---|
| 2,197,973 | 4/1940 | Everett et al. | 2/13 |
| 2,233,698 | 3/1941 | Girouard | 2/206 |
| 2,363,557 | 11/1944 | Schauweker | 2/9 |
| 2,364,354 | 12/1944 | Felch | 2/9 |
| 3,346,875 | 10/1967 | Weisberger | 2/9 |
| 3,613,116 | 10/1971 | Stroup | 2/12 |
| 4,387,471 | 6/1983 | Hsu et al. | 2/909 |
| 4,674,133 | 6/1987 | Oschner | 2/9 |
| 4,852,189 | 8/1989 | Duggan | 2/13 |
| 5,123,115 | 6/1992 | Braswell-Moore | 2/909 |
| 5,167,036 | 12/1992 | Daprato | 2/9 |
| 5,274,847 | 1/1994 | Lauttamus | 2/9 |

OTHER PUBLICATIONS

Gershman, Maurice. "Self-Adhering Nylon Tapes", *Journal of AMA*, vol. 168, No. 7, Oct. 18, 1958.

Primary Examiner—Clifford D. Crowder
Assistant Examiner—Amy Brooke Vanatta
Attorney, Agent, or Firm—Frank D. Gilliam; John R. Duncan

[57] ABSTRACT

A sun shield or nose guard for eyeglasses, such as sunglasses or goggles, which is readably attachable and removable from the glasses. The sun shield is formed from a thin, semi-stiff but flexible sheet material, such as a suitable plastic, to the general shape of a human nose. A small piece of hook-and-loop fastener material of the sort available under the Velcro trademark, is secured to the upper, outer, edge of the sun shield, preferably by an adhesive. A corresponding piece of the complementary hook-and-eye material is secured to the glasses between the glasses' nose pads, preferably by an adhesive. Such pieces can be attached to a number of different glasses so that the sun shield can be selectively used with any of them. The sun shield can be easily attached for use when needed and detached when not needed or when it is desired to attach the shield to a different pair of glasses. A rounded bead is provided around the periphery of the sun shield for maximum comfort wherever the edge may contact the nose. The piece of hook-and-eye material attached to the sun shield may overlap the edge of the sun shield, with about 30 to 70% of the piece beyond the edge, to provide optimum flexibility.

14 Claims, 1 Drawing Sheet

U.S. Patent  May 23, 1995  5,416,923
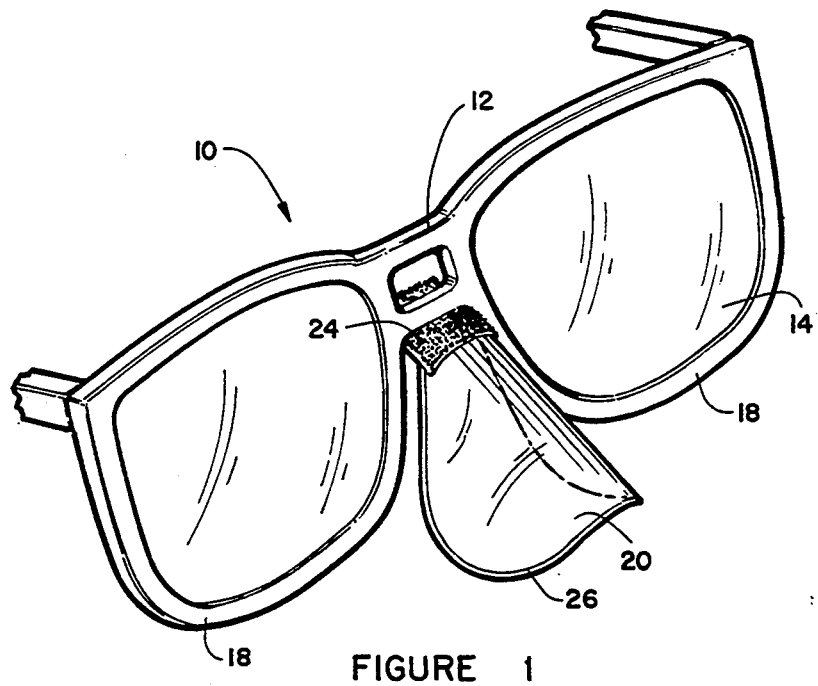
FIGURE 1
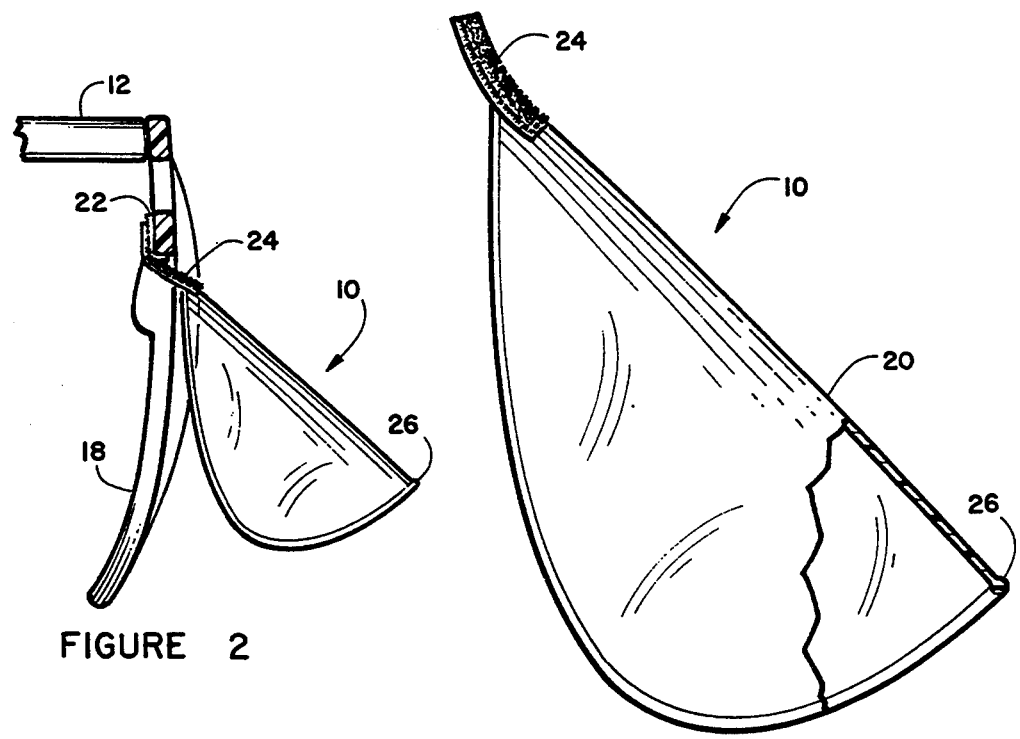
FIGURE 2
FIGURE 3

REMOVABLE NOSE SUN SHIELD FOR EYEGLASSES

BACKGROUND OF THE INVENTION

This invention relates in general to the protection of human noses from the effects of exposure to the sun and, more particularly, to a sun shield removably attachable to eyeglasses to shield the nose from sunlight.

As is well known, the skin of the nose is particularly sensitive to intense sunlight, which can cause severe sunburn, to the extent that the skin is blistered, and eventually permanent skin damage and possibly skin cancer.

Hats of various kinds are often worn to protect the skin of the face and nose from excessive sun exposure. However, in environments with considerable reflected sunlight, such as beaches and snow conditions, hats are not fully effective. Hats cannot be easily worn during some outdoor activities, such as surfing or beach volleyball.

Sunscreen lotions and various ointments, such as zinc oxide, are sometimes applied to the nose as a protection against sun exposure. While generally effective if properly used, some people are sensitive to some ingredients in these lotions and ointments and suffer an allergic reaction. On hot, humid, days perspiration may wash away the protective film, without the person being aware of the loss of protection. If the person is swimming or surfing, protection is rapidly lost. Thus, under many conditions these agents may provide only limited, short time, protection.

A number of different nose guards or sun shields have been developed over the years to provide more positive and certain protection to the skin of the nose. Some, such as that disclosed by Harris in U.S. Pat. No. 1,761,664 mechanically clip to the nose. These nose shields are uncomfortable to wear and tend to come loose with vigorous exercise. Others, such as those described by Sanderson in U.S. Pat. Nos. 3,594,813 and Oschner in 4,674,133 bond the shield to the nose skin with an adhesive. Again, the adhesive tends to be uncomfortable and to release its grip when exposed to perspiration or water while swimming.

Many nose shields are secured to eyeglasses, including sunglasses or goggles, in one way or another. For example, Gongoll in U.S. Pat. No. 3,007,173 fasten a shield to glasses with a cumbersome buckle and strap arrangement. Daprato, in U.S. Pat. No. 5,167,036, fastens a nose shield to glasses with a complex arrangement of perforated backing plate and cords. These arrangements cannot be easily installed and removed when sun conditions change. Maurice in U.S. Pat. 1,048,191 describes a nose clip to hold a nose shield in place with pince-nez glasses. The clip arrangement would obviously be quite uncomfortable.

The prior nose shields were often formed from a thin flat sheet of plastic material such as celluloid. The edges of these thin sheets tend to irritate the abutting nose skin surfaces. Further, these prior shields tend to fit only certain styles of glasses and the attachment means is not sufficiently flexible to allow the shield to lie smoothly against the nose without excessive pressure.

Thus, there is a continuing need for comfortable, effective, nose shields that can be easily and quickly installed on and removed from a variety of different styles of glasses.

SUMMARY OF THE INVENTION

The above noted problems, and others, are overcome in accordance with this invention by a nose sun shield which comprises a thin sheet of material, preferably a plastic material, formed into a shape generally in accordance with the human nose having a first end adapted to conform to the bridge of a nose. A small piece of hook-and-loop material, either the hook piece or the complementary loop piece, is secured to the outer surface of said first end, preferably extending past the edge of the sheet. A second small piece of hook-and-loop material complementary to the piece secured to the sheet has a self-adhesive coating on the back. The self adhesive coating is covered with a protective, removable, cover sheet.

In use, the second piece of hook-and-loop material is separated from the cover sheet and the self adhesive surface is pressed against an appropriate location on the bridge, between the nose pads, of suitable eyeglasses. For the purposes of this application, "eyeglasses" will be understood to include sunglasses, goggles and the like. In one particularly desirable method of applying the second piece of hook-and-loop material to the eyeglasses the second piece is held by the hook and loop material to the first piece which is secured to the sun shield sheet. The cover sheet is removed and the sun shield sheet is positioned in the desired final location with the self-adhesive layer in contact with the bridge or similar area on the glasses. After the adhesive has been allowed to bond for a suitable period, the sun shield can be removed by separating the two pieces of hook-and-loop material. Thereafter, the sun shield may be reinstalled and removed as desired.

Preferably, the shield has a rounded edge around the periphery having a bead-like cross section. For best results, the beaded edge has a diameter from about 1.5 to 5 times the thickness of the sheet making up the shield.

Accordingly, it is an object of this invention to provide a nose sun shield which is comfortable to use, with the shield lightly held at or near the nose without excessive pressure and without edges digging into the wearer's skin. Another object is to provide a nose sun shield that can be easily fastened to any of a large variety of eyeglass designs and easily removed and replaced as desired when sun conditions or other factors change. A further object is to provide a nose sun shield that can be quickly and easily moved from one pair of glasses to another, e.g. from reading glasses to sunglasses, simply by providing a piece of the correct hook-and-loop material on each pair.

BRIEF DESCRIPTION OF THE DRAWING

Details of the invention, and of certain preferred embodiments thereof, will be further understood upon reference to the drawing, wherein:

FIG. 1 is a schematic front perspective view showing the nose sun shield in place on a pair of eyeglasses;

FIG. 2 is a schematic perspective view showing the glasses of FIG. 1 from the inside with the sun shield detached; and FIG. 3 is a detail section view taken on line 3—3 in FIG. 1.

DETAILED DESCRIPTION OF PREFERRED EMBODIMENTS

As seen in FIGS. 1 and 2, glasses 10 typically have a bridge 12 between the lenses 14 that lies adjacent to, but spaced from, the bridge of a wearer's nose when the glasses are worn. Conventional pads 16 for locating the glasses on the wearer's nose are secured to the lens frame 18 near bridge 12. Pads 16 typically are formed as protuberances on frame 18 or may be mounted on short, stiff but bendable, wires extending from frame 18. As seen, a protective sun shield 20 is flexibly connectable to bridge 12 by a first piece 22 of hook-and-loop material secured to bridge 12 and a second, complementary, piece 24 of hook-and-loop material secured to sun shield 20.

The first and second pieces 22 and 24 include one piece of "hook" material and one piece of "loop" material. These pieces of hook-and-loop material, of the type sold under the Velcro trademark, are securely held together when pressed together and release easily when firmly pulled apart.

Sun shield 20 is basically formed from a thin, flat sheet of material that is permanently deformed into a shape corresponding to a human nose. Any suitable material may be used in sun shield 20. Light metals such as aluminum, plastics such as vinyl, acrylics and polycarbonates may be used. Of these, polycarbonates are preferred because of its hard, smooth surface and ease of forming into the desired shape by thermal means. Typical polycarbonate films are available from the General Electric Company under the "Lexan" trademark. The material or color should not transmit significant incident ultraviolet radiation. The material may absorb or reflect ultraviolet radiation. The material may have a reflective coating, such as vacuum evaporated aluminum. Or, a conventional ultraviolet absorbing agent may be incorporated in the sun shield material or in a coating thereon. The sun shield may be in any suitable color, including any desired color pattern, so long as ultraviolet radiation is not significantly transmitted.

Any suitable hook-and-loop material, in any desired color, may be used. The first and second pieces 22 and 24, respectively, may have any suitable dimensions. While both may have the same dimensions, in some cases it is preferred that first piece 22, secured to the bridge of the glasses, be slightly larger to aid in removal without inadvertently removing the first strip from the glasses. In general, strips having lengths from about ⅜ to ¾ inch and widths from about ⅛ to ⅜ inch are preferred.

Any suitable means may be used to secure first pieces 22 to the bridge of glasses and second pieces 24 to sun shield 20. The self-adhesive coatings provided by manufacturers of hook-and-loop material are preferred for maximum efficiency. Other flexible adhesives, such as latex based contact cements may be used.

While the second piece 24 of hook-and-loop material could be fastened to sun shield 20 with the entire second piece in contact with the sun shield surface, for optimum performance it is preferred that from about 30 to 70% of second piece 24 extend beyond the edge of the sun shield. When pressed against the first piece 22 on the glasses, second piece acts as a slightly stiff hinge, pivotable about the line of contact. Thus, the stiffness will press the sun shield lightly against the wearer's nose, while providing flexibility to accommodate different glasses design and different nose shapes.

If a pre-coated second piece 24 is used, there will be a self adhesive layer exposed on the back of the portion of the second piece which extends beyond the edge of sun shield 20. Ordinarily, this is not a problem and may be ignored. If desired, a small amount of dry powder, such as talcum powder or the like, may be applied to this edge to eliminate the tackiness. Or, instead of pre-coated adhesive over the entire back surface of second piece 24, only that area that is to be secured to sun shield 20 could be coated with adhesive.

Prior art nose guards have often had problems with the edge of a thin sheet digging into the adjacent surface of the nose or cheeks when the guard is in use. To avoid any such problems, it is preferred that the periphery of sun shield 24 have a rounded edge 26 with a bead-like configuration, as seen in section in FIG. 3.

The sun shield and mounting means of this invention is adaptable to most designs of glasses, including clear and sun glasses and many types of goggles. With goggles that have a cover surrounding the lenses and closely approaching the face and nose near the nose bridge, the first piece 22 of hook and loop material can be secured to the goggles where the cover crosses the nose, even where that surface is perpendicular to the nose, since the flexible portion of the second piece 24 extends beyond the edge of sun shield 20 and can be bent back as necessary. In some stylized sunglasses, where both lenses are formed from a single piece of sheet material that includes a narrowed portion extending across the nose bridge area, first piece 22 could be secured to the back surface of the narrowed portion adjacent to the nose bridge.

In use, sun shield 20 will be ordinarily purchased with second piece 24 of hook-and-loop material bonded to the sun shield, with the first piece 22 held to the second piece by the hooks and loops. The back side of the first piece will have a coating of self adhesive material, protected by an easily removable cover sheet. The purchaser can select the proper position for the sun shield by positioning the assembly against his or her glasses with the protective cover in place. Once the desired position is selected, the cover sheet is removed and the assembly used to press the first piece in place on the glasses. The sun shield is then ready for use. When the user desires to remove sun shield, such as when going indoors, the sun shield is easily removed by separating the hook-and-loop connection.

Other applications, variations and ramifications of this invention will occur to those skilled in the art upon reading this disclosure. Those are intended to be included within the scope of this invention, as defined in the appended claims.

I claim:

1. A sun shield for protecting a human nose from ultraviolet radiation from the sun which comprises;

a sheet of thin, flexible material configured to approximate the shape of the surface of a human nose;

said sheet having a first edge portion corresponding to the bridge of a human nose;

said sheet including material reducing transmission of incident ultraviolet light;

a first piece of hook-and-loop material having a self adhesive layer on one surface and a hook or loop other surface;

a second piece of hook-and-loop material secured to said sheet at said first edge portion with from about 30 to 70% of said piece extending beyond said first edge, said second piece having either a hook or loop exposed surface said hook or loop surface positioned opposite that of said second piece; and said first piece being securable by said adhesive layer to the bridge region of glasses so that said first piece may be engaged with said second piece to cover the nose of a person wearing said glasses.

2. The sun shield according to claim 1 wherein the peripheral edge of said sheet has a continuous rounded bead.

3. The sun shield according to claim 2 wherein said bead edge has a diameter of from about 1.5 to 5 times the thickness of said sheet.

4. The sun shield according to claim 1 wherein said sheet is formed from a plastic selected from the group consisting of vinyls, acrylics and polycarbonates.

5. The sun shield according to claim 1 wherein each of said first and second pieces of hook-and-loop material has a length of from about ⅜ to ¾ inch and a width of from about ⅛ and ⅜ inch.

6. The sun shield according to claim 5 wherein said second piece of hook-and-loop material has a length from about 5 to 25% longer than the length of said first piece.

7. A sun shield assembly for application to eyeglasses for protecting a human nose from ultraviolet radiation from the sun which comprises:

a sheet of thin, flexible material configured to approximate the shape of a human nose;

said sheet having a first edge portion corresponding to the bridge of a human nose;

said sheet reducing transmission of incident ultraviolet light;

a first piece of hook-and-loop material having a self adhesive layer on one surface and a hook or loop other surface;

a second piece of hook-and-loop material secured to said sheet at said first edge portion with from about 30 to 70% of said piece extending beyond said first edge, said second piece having either a hook or loop exposed surface said hook or loop surface positioned opposite that of said second piece;

said second piece releasably held to said first piece by the cooperation of said hook-and-loop material, a removable cover sheet protecting said self adhesive layer;

whereby said sun shield assembly may be selectively positioned relative to the bridge area of a pair of eyeglasses, the protective cover sheet removed and the second sheet bonded to said bridge area in said selected position.

8. The sun shield assembly according to claim 7 wherein said second piece is held to said first piece with the widths of the two pieces substantially co-extensive.

9. The sun shield assembly according to claim 7 wherein the peripheral edge of said sheet has a continuous rounded bead.

10. The sun shield assembly according to claim 9 wherein said bead edge has a diameter of from about 1.5 to 5 times the thickness of said sheet.

11. The sun shield assembly according to claim 7 wherein said sheet is formed from a plastic selected from the group consisting of vinyls, acrylics and polycarbonates.

12. The sun shield assembly according to claim 7 wherein each of said first and second pieces of hook-and-loop material has a length of from about ⅜ to ¾ inch and a width of from about ⅛ and ⅜ inch.

13. The sun shield assembly according to claim 12 wherein said second piece of hook-and-loop material has a length from about 5 to 25% longer than the length of said first piece.

14. The method of installing a sun shield on eyeglasses to protect the wearer's nose from ultraviolet radiation from the sun which comprises the steps of:

providing a sun shield assembly which comprises a sheet of thin flexible material shaped to conform to the general shape of a human nose, a first piece of hook-and-loop material bonded to an edge of said shield conforming to the bridge of a nose, a cooperating second piece of hook-and-loop material held to said first piece by said hooks and loops, the opposite side of said second piece bearing a self adhesive layer protected by a removable cover sheet;

selectively positioning said sun shield assembly with the cover sheet against the bridge of a pair eyeglasses to select an optimum location;

removing said cover sheet;

returning said sun shield assembly to the selected position; and pressing said self adhesive layer against the bridge of said eyeglasses;

whereby said sun shield is removably and replaceably secured in the selected position on said eyeglasses.

* * * * *